United States Patent
Howard

(10) Patent No.: US 9,238,120 B2
(45) Date of Patent: Jan. 19, 2016

(54) METHODS AND APPARATUS FOR INTRAVENOUS TUBING

(71) Applicant: Thomas Austin Howard, Savannah, GA (US)

(72) Inventor: Thomas Austin Howard, Savannah, GA (US)

(*) Notice: Subject to any disclaimer, the term of this patent is extended or adjusted under 35 U.S.C. 154(b) by 0 days.

(21) Appl. No.: 14/261,249

(22) Filed: Apr. 24, 2014

(65) Prior Publication Data

US 2015/0306344 A1     Oct. 29, 2015

(51) Int. Cl.
*F16L 9/18* (2006.01)
*A61M 25/00* (2006.01)
*A61M 39/10* (2006.01)

(52) U.S. Cl.
CPC ............ *A61M 25/0021* (2013.01); *A61M 39/10* (2013.01); *A61M 2025/0042* (2013.01); *A61M 2207/00* (2013.01)

(58) Field of Classification Search
CPC . A61M 25/0026; B29C 65/1432; F16L 11/22
USPC .............................. 138/115, 116, 109; 604/43
See application file for complete search history.

(56) References Cited

U.S. PATENT DOCUMENTS

| | | | | |
|---|---|---|---|---|
| 1,114,268 A * | 10/1914 | Kells | ................ | 604/28 |
| 2,020,860 A * | 11/1935 | Touborg | .......................... | 62/277 |
| 2,122,335 A * | 6/1938 | Berman et al. | ........... | 156/244.14 |
| 2,624,366 A * | 1/1953 | Pugh | .............................. | 138/115 |
| 4,064,355 A * | 12/1977 | Neroni et al. | .................... | 174/47 |
| 4,086,937 A * | 5/1978 | Hechler, IV | .................. | 137/559 |
| 5,224,674 A | 7/1993 | Simons | | |
| 5,336,220 A * | 8/1994 | Ryan et al. | ....................... | 604/22 |
| 5,707,351 A * | 1/1998 | Dorsey, III | ...................... | 604/30 |
| 6,190,349 B1 * | 2/2001 | Ash et al. | ......................... | 604/43 |
| 6,315,759 B1 | 11/2001 | Peterson | | |
| 8,585,950 B2 * | 11/2013 | Appling et al. | ................ | 264/248 |
| 2004/0092863 A1 * | 5/2004 | Raulerson et al. | ............... | 604/43 |
| 2004/0135039 A1 | 7/2004 | Reichert et al. | | |
| 2006/0025702 A1 | 2/2006 | Sterrantino et al. | | |
| 2009/0209940 A1 * | 8/2009 | Nimkar et al. | ................. | 604/523 |

* cited by examiner

*Primary Examiner* — Patrick F Brinson
(74) *Attorney, Agent, or Firm* — Sorell, Lenna & Schmidt, LLP

(57) ABSTRACT

The present invention provides, among other things, a tubing apparatus that allows for better organization of tubes within a system by permanently coupling medical tubes. Generally, this invention comprises a primary tube and a secondary tube, wherein the secondary tube is permanently coupled to the primary tube at least partially along the secondary tube's length. The primary tube comprises at least one coupling port to which one end of the secondary tube fluidly couples.

20 Claims, 3 Drawing Sheets

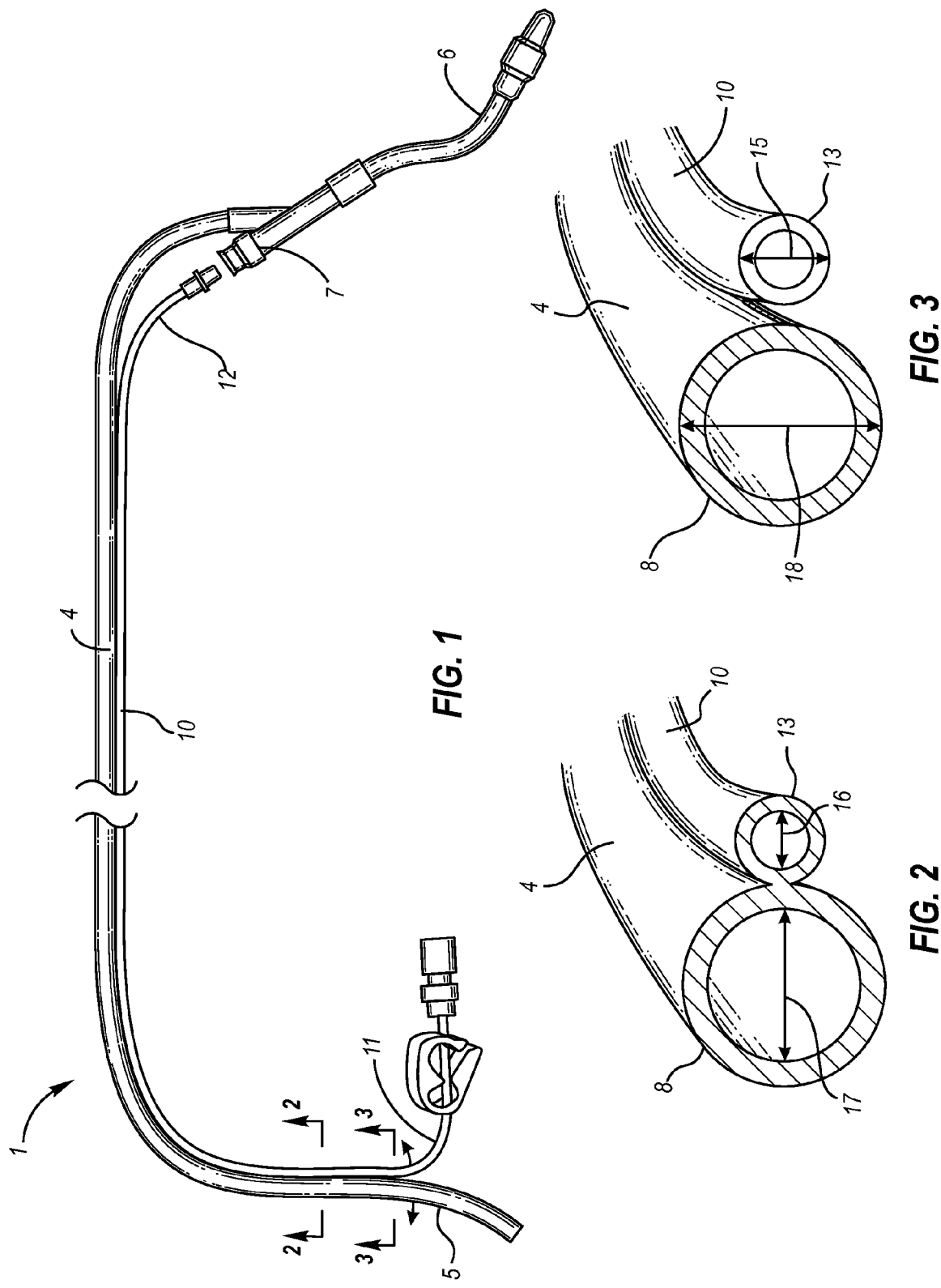

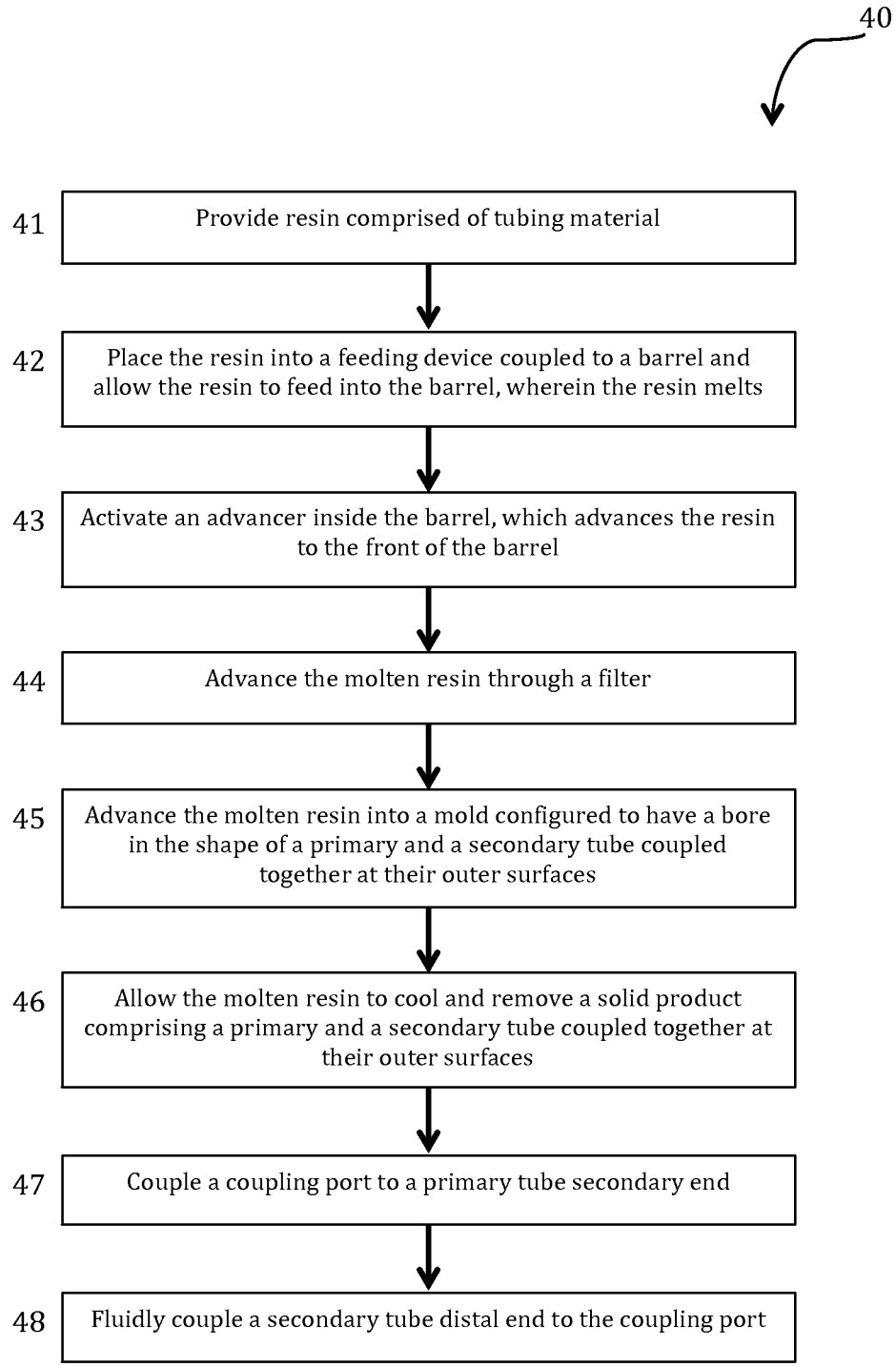

METHODS AND APPARATUS FOR INTRAVENOUS TUBING

BACKGROUND

1. Field of the Invention

This invention pertains generally to tubing products, and more specifically, to tubing for medical purposes, such as intravenous tubing, but it is not limited to that field.

2. Description of Related Art

In medical settings, patients often require the intravenous administration of medication and nutrients through the use of intravenous tubes ("IV tubes"). It is not uncommon for hospital patients to have more than one standard IV tube that administers an electrolyte solution, and each standard IV tube has injection ports to which secondary tubes can be connected in order to administer specific medications. All of these tubes are long and often get in the way of one another, causing entanglement and confusion as to which tube is which. The mess of tubing can become difficult to navigate and poses a risk to the patient if the tubes cannot be organized and identified in a time-sensitive situation.

Also, in some circumstances, the administration of additional medication is needed immediately. However because most IV tubes, including secondary tubes, have long lengths, the medication may not reach the patient as quickly as desired because of all of the tubing through which the medication has to travel before reaching the patient.

There are existing products whose aim is to organize and/or protect IV tubes. Some products simply bundle tubes together, as described in U.S. Pat. No. 6,315,759, and some simply clip tubes together at one point, but leave the rest of the long tubing straying around a patient (U.S. Publication No. 2004/0135039).

So as to reduce the complexity and length of the Detailed Specification, and to fully establish the state of the art in certain areas of technology, Applicant herein expressly incorporates by reference all of the following materials identified in each numbered paragraph below.

U.S. Publication No. 2004/0135039, Reichert, "Controlling and identifying system of holders for intravenous lines and other elongated members." This reference describes a clip that couples multiple IV tubes together at one point.

U.S. Pat. No. 5,224,674, Simons, "Method and apparatus for organizing and identifying intravenous administration lines." This reference describes a device which couples multiple IV tubes together and provides a place on the device to label each tube.

U.S. Publication No. 6,315,759, Peterson, "Protective cover for intravenous lines and other elongated members." This reference describes a device that bundles multiple IV tubes together and also protects them from external forces because it is comprised of resilient material.

Applicant believes that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), Applicant will amend the specification to expressly recite the essential material that is incorporated by reference as allowed by the applicable rules.

SUMMARY

The present invention provides, among other things, a tubing apparatus that allows for better organization of tubes within a system by permanently coupling tubes. Generally, this invention comprises a primary tube and a secondary tube, which is permanently coupled to the primary tube at least partially along the secondary tube's length. The primary tube comprises at least one coupling port, to which a distal end of the secondary tube fluidly couples.

The secondary tube may be permanently coupled to the primary tube at either end of the secondary tube, both ends of the secondary tube, the mid section of the secondary tube, or intermittently along the secondary tube.

The primary tube may be a standard IV tube, and the secondary tube may be a microbore IV tube, which has an internal diameter less than that of the primary tube (a standard IV tube); the secondary tube (microbore IV tube) internal diameter may be 0.3 millimeters to 1.3 millimeters. These two tubes being permanently coupled allows for better organization of the IV tubes in a medical setting. Also, the secondary tube may be of a shorter length than the primary tube; the secondary tube length may be within a range of 2 to 5 feet long. If the secondary tube is for the administration of medication, by making the secondary tube shorter, the distance any medication has to travel through the tube to reach the patient is less. Accordingly, time-sensitive medication, during an operation, for example, will be administered much faster than having to travel through longer tubing.

Aspects and applications of the invention presented herein are described below in the drawings and detailed description of the invention. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographer, to use only the plain and ordinary meaning of terms in the specification and claims unless he clearly states otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of pre-AIA 35 U.S.C. §112, ¶6 and post-AIA 35 U.S.C. §112(f). Thus, the use of the words "function," "means" or "step" in the Detailed Description or Description of the Drawings or claims is not intended to somehow indicate a desire to invoke the special provisions of pre-AIA 35 U.S.C. §112, ¶6 or post-AIA 35 U.S.C. §112 (f), to define the invention. To the contrary, if the provisions of pre-AIA 35 U.S.C. §112, ¶6 or post-AIA 35 U.S.C. §112(f) are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventor not to invoke the provisions of pre-AIA 35 U.S.C. §112, ¶6 or post-AIA 35 U.S.C. §112(f). Moreover, even if the provisions of pre-AIA 35 U.S.C. §112, ¶6 or post-AIA 35 U.S.C. §112(f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

The foregoing and other aspects, features, and advantages will be apparent to those artisans of ordinary skill in the art from the DETAILED DESCRIPTION and DRAWINGS, and from the CLAIMS.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

FIG. 1 depicts a perspective view of an embodiment of a tubing apparatus with a primary tube permanently coupled to a secondary tube.

FIGS. 2-3 depict perspective views of cross sections of embodiments of a tubing apparatus.

FIG. 5 depicts another flow diagram of a method of manufacturing an embodiment of a tubing apparatus.

Figure 4:
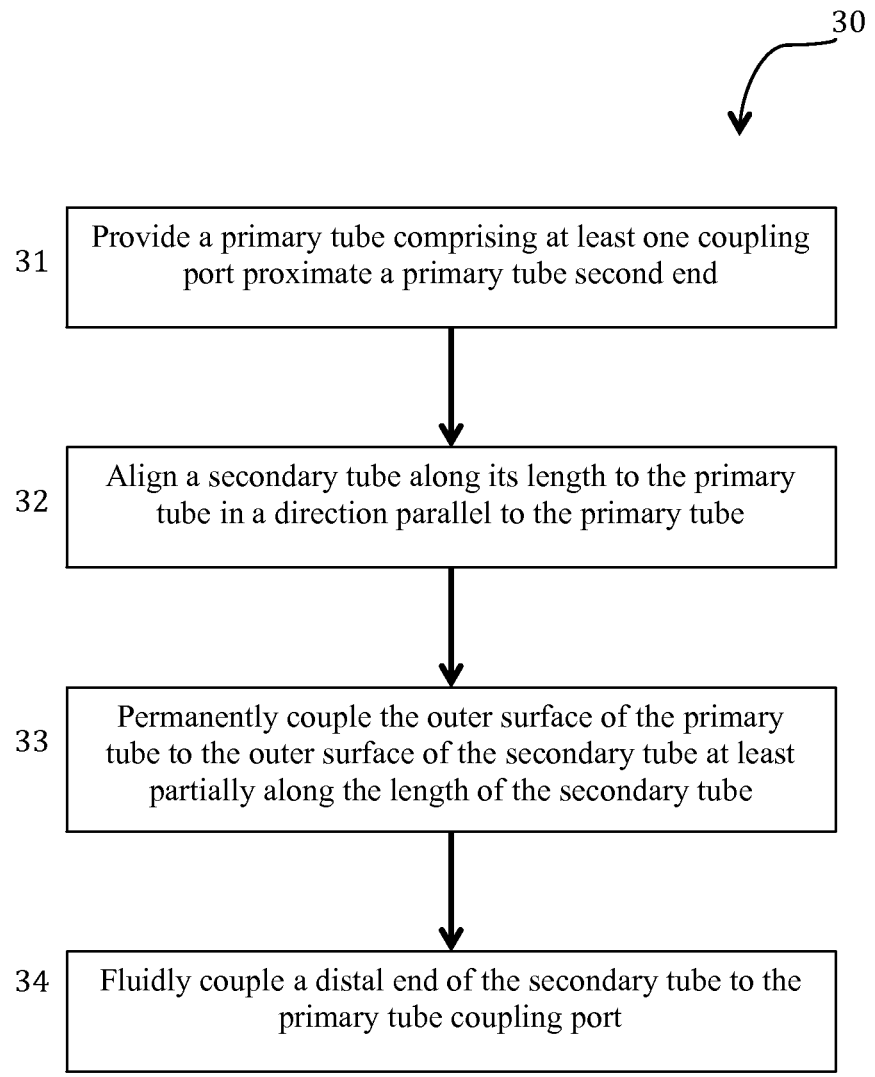
FIG. 4 depicts a flow diagram of a method of manufacturing an embodiment of a tubing apparatus.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. It should be noted that there are many different and alternative configurations, devices and technologies to which the disclosed inventions may be applied. The full scope of the inventions is not limited to the examples that are described below.

Currently, IV tubes are sold as individual tubes, and the tubes sold often are very long. Because patients often need multiple IV tubes, there can be a mess of IV tubing around a patient causing entanglement and confusion. Existing ways to organize or clip tubes together are inadequate. With clips that couple IV tubes together at specific points on the tubing, the IV tubes separate where they are not coupled by a clip and still have great potential to entangle. This may happen even if multiple clips are used. Also, doctors and nurses do not have time to couple tubes together before use with patients. This invention allows two or more IV tubes to come as a single product, in which the tubes are permanently coupled. This results in much better organization of tubing and less confusion. Regarding tube length, based on the need, one or more of the tubes that are permanently coupled to one another may come in certain lengths that are most convenient for their use in certain medical settings. For example, a microbore tube may come permanently coupled to a standard IV tube, wherein the microbore tube may be of a significantly shorter length than the standard IV tube. This may allow the microbore tube end, to which the doctor needs easy access, to rest near the patient's bed without a mess of extra tubing between that end and the other tube end near the patient's vein.

In the current embodiment, as depicted in FIGS. 1-3, tubing apparatus 1 may comprise a primary tube 4 and a secondary tube 10, wherein the secondary tube 10 may be permanently coupled at least partially along its length to the primary tube 4 in a direction that is parallel to the primary tube 4.

The primary tube 4 may comprise a first end 5, a second end 6 opposite the first end 5, at least one coupling port 7 proximate to the second end 6, and an outer surface 8. The primary tube 4 may be a standard IV tube, wherein the primary tube first end 5 is coupled to an IV bag filled with fluid (not pictured), and the primary tube second end 6 may be coupled to a catheter (not pictured), which may be inserted into a patient for intravenous administration of fluid, medication, etc. The coupling port 7 may be closer to primary tube second end 6 than it is to the primary tube first end 5, or vice versa, without exceeding the scope of this invention. There may be additional coupling ports along the primary tube 4 and any of those coupling ports may be proximate to either the primary tube first end 5 or primary tube second end 6.

The primary tube 4 may be of any cross-sectional shape, which would allow the secondary tube 10 to couple to it (rectangular, circular, triangular, etc.). The primary tube 4 may be of any suitable length, but in the current embodiment, it may be of a length that is greater than or equal to the secondary tube 10. The primary tube 4 may be comprised of any material that is rigid but also flexible such as polyethylene, polyvinylchloride, or a combination of the two.

The secondary tube 10 may comprise a proximal end 11, a distal end 12 opposite the proximal end 11, and an outer surface 13, wherein the secondary tube distal end 12 may be fluidly-coupled to the primary tube coupling port 7 proximate to the primary tube second end 6. The secondary tube 10 may be permanently coupled on its outer surface 13 along its length to the primary tube outer surface 8 in a direction that is parallel to the primary tube 4. The secondary tube outer surface 13 may be permanently coupled to the primary tube outer surface 8 along any of the sections of the secondary tube 10. For example, the secondary tube outer surface 13 may be coupled along its length to the primary tube outer surface 8 only at the secondary tube proximal end 11, only at the secondary tube distal end 12, or both without be coupled between the ends, or only coupled to the primary tube outer surface 8 at a section in between the secondary tube proximal 11 and distal 12 ends. The secondary tube outer surface 13 may also be permanently coupled intermittently along its length to the primary tube outer surface 8. The secondary tube outer surface 13 may be permanently-coupled on top of, below, to the side of, or spiraling around the primary tube outer surface 8, or in any other suitable configuration. The secondary tube proximal end 11 may be configured to couple with a syringe or other device to administer fluid, liquid, medicine, etc.

The secondary tube 10 may be of any cross-sectional shape, which would allow it to couple to the primary tube 4 (rectangular, circular, triangular, etc.). The secondary tube 10 may be of any suitable length, but in the current embodiment, the secondary tube 10 comprises a shorter length than the primary tube 4. However, it would not be outside the scope of this invention to have the lengths of the primary and secondary tubes being equal. The secondary tube 10 may be comprised of any material that is rigid but also flexible such as polyethylene, polyvinylchloride, or a combination of the two. It is also within the scope of this invention to have the primary tube and secondary tube being permanently coupled, but not having the secondary tube distal end fluidly couple to a coupling port on the primary tube. This embodiment would also decreasing entanglement but would comprise two or more permanently coupled, separate tubes.

Depicted in FIGS. 2 and 3, the secondary tube 10 may have an internal diameter 16 that is smaller than the primary tube internal diameter 17, and/or an external diameter 15 that is smaller than the primary tube external diameter 18. That is, in the current embodiment, the secondary tube 10 may be a microbore tube, meaning that it has a smaller internal diameter 16 than a standard IV tube (the current embodiment depicts the primary tube 4 as a standard IV tube). Microbore tubing may have an internal diameter 16 of approximately 0.3 millimeters to 1.3 millimeters. It would not be outside the scope of this invention if the internal and external diameters of the primary tube 4 and secondary tube 10 were the same size, meaning that both the primary tube 4 and secondary tube 10 may be microbore tubes or standard IV tubes or any other type of tube.

FIGS. 2 and 3 also provide depictions of the coupling of the primary tube 4 and the secondary tube 10 along cross sections 2 and 3 in FIG. 1, respectively.

FIG. 4 depicts a flow diagram of a first method 30 of manufacturing the tubing apparatus 1, which may comprise the steps described in blocks 31-34. Block 31 of the method describes a step that may comprise providing a primary tube 4, comprising at least one coupling port 7 proximate to the primary tube second end 6. The primary tube 4 may comprise more than one coupling port, and it would not be outside the scope of this invention for a single coupling port to be located on the primary tube 4 in a location other than the primary tube second end 6.

Block 32 describes a step that may comprise aligning the secondary tube 10 along its length to the primary tube 4 in a direction parallel to the primary tube 4. The secondary tube outer surface 13 may be aligned on top of, below, to the side of, or spiraling around the primary tube outer surface 8, or in any other suitable configuration.

Block 33 describes a step that may comprise permanently coupling the primary tube outer surface 8 to the secondary tube outer surface 13 at least partially along the length of the secondary tube 10. As described above, the secondary tube outer surface 13 may be permanently coupled to the primary tube outer surface 8 along any of the sections of the secondary tube 10. For example, the secondary tube outer surface 13 may be coupled along its length to the primary tube outer surface 8 only at the secondary tube proximal end 11, only at the secondary tube distal end 12, or both without be coupled between the ends, or only coupled to the primary tube outer surface 8 at a section in between the secondary tube proximal 11 and distal 12 ends. The secondary tube outer surface 13 may also be permanently coupled intermittently along its length to the primary tube outer surface 8. The primary and secondary tubes may be permanently coupled using any suitable method such as an adhesive, or a process comprising melting the outer surfaces of the tubes, touching them, and allowing the outer surface of the tubes to fuse together.

Finally, block 34 describes a step that may comprise fluidly coupling the secondary tube distal end 12 to the primary tube coupling port 7. These steps may be performed in any suitable order to make the tubing apparatus.

FIG. 5 depicts a flow diagram of a second method 40 of manufacturing the tubing apparatus 1, which may comprise the steps described in blocks 41-48. Block 41 describes a step that may comprise providing resin comprised of tubing material. Resin are small beads of solid material that may take on any suitable shape. The resin may be comprised of any material that is rigid but also flexible such as polyethylene, polyvinylchloride, or a combination of the two.

Block 42 describes a step that may comprise placing the resin into a feeding device coupled to a barrel and allowing the resin to feed into the barrel, wherein the resin melts. The feeding device may be a container comprising an open top, a hollow interior configured to store material, and an open bottom to feed the material into another area, which is, in this case, the barrel. The feeding device may be a hopper, funnel, tube, or any other thing that is capable of holding material and depositing it in another place. The feeding device may be as simple as someone's hands. The barrel is a container in which the resin melts into liquid form, and may be any suitable shape comprising a hollow interior.

Block 43 describes a step that may comprise activating an advancer inside the barrel, which advances the resin to the front of the barrel. The advancer may be a rotating screw comprising a bar with threading on the outside so when the resin enter the barrel, they are caught by the threading that is being rotated, and the resin is then advanced forward. Any other device suitable to advance the resin within the barrel may also be used, such as a conveyor belt or some sort of pressure system using springs, air, or any other force.

The molten resin may then be advanced through a filter such as a breaker plate, as described in block 44. The filter may be of any suitable shape and material to allow the molten resin to pass therethrough while filtering out any contaminants in the molten resin.

The molten resin may then be advanced into a mold, or die, configured to have a bore in the shape of a primary tube and a secondary tube coupled together at their outer surfaces as described in block 45. The secondary tube 10 may be permanently coupled on its outer surface 13 at least partially along its length to the primary tube outer surface 8 in a direction that is parallel to the primary tube 4. The secondary tube outer surface 13 may be permanently coupled to the primary tube outer surface 8 along any of the sections of the secondary tube 10. For example, the secondary tube outer surface 13 may be coupled along its length to the primary tube outer surface 8 only at the secondary tube proximal end 11, only at the secondary tube distal end 12, or both without be coupled between the ends, or only coupled to the primary tube outer surface 8 at a section in between the secondary tube proximal 11 and distal 12 ends. The secondary tube outer surface 13 may also be permanently coupled intermittently along its length to the primary tube outer surface 8. The secondary tube outer surface 13 may be permanently coupled on top of, below, to the side of, or spiraling around the primary tube outer surface 8, or in any other suitable configuration. The mold may be comprised of any suitable material to remain rigid in order to form the molten resin into the desired shape.

Block 46 describes a step that may comprise allowing the molten to cool and solidify, forming the solid product comprising a primary tube 4 permanently coupled to secondary tube 10 at least partially along the length of the secondary tube 10. The solid product would then be removed from the mold.

As described in block 47, a coupling port may then be coupled to the primary tube second end 6. Additional coupling ports may be coupled to the primary tube 4 without going outside the scope of this invention. It is not necessary that the coupling port be coupled at the primary tube second end 6, but this is the current embodiment shown in FIG. 1. Finally, block 48 describes the concluding step, which may comprise fluidly coupling the secondary tube distal end 12 to the primary tube coupling port 7. These steps may be performed in any suitable order to make the tubing apparatus.

I claim:

1. A tubing apparatus, comprising:
   a flexible primary tube having a first length and configured to intravenously deliver fluid to a patient, comprising:
     a first end;
     a second end opposite the first end; and
     at least one coupling port proximate the second end; and
   a flexible secondary tube having a second length, the second length being shorter than the first length, comprising:
     a proximal end configured to couple with a device to administer fluid to a patient; and
     a distal end fluidly-coupled to the flexible primary tube coupling port,
   wherein only an outer surface of the flexible secondary tube is permanently coupled at least partially along its length only to an outer surface of the flexible primary tube and the flexible secondary tube runs in a direction parallel to the flexible primary tube, and
   wherein the flexible primary tube and the flexible secondary tube each include a uniform circumferential inner surface.

2. The apparatus of claim 1, wherein the flexible secondary tube is permanently coupled only at its distal end to the primary tube.

3. The apparatus of claim 1, wherein the flexible secondary tube is permanently coupled only at its proximal end to the primary tube.

4. The apparatus of claim 1, wherein the flexible secondary tube is permanently coupled only at its distal and proximal ends to the flexible primary tube.

5. The apparatus of claim 1, wherein the flexible secondary tube is permanently coupled only at a portion between its proximal and distal ends to the flexible primary tube.

6. The apparatus of claim 1, wherein the flexible secondary tube is coupled intermittently along its length to the flexible primary tube.

7. The apparatus of claim 1, wherein the length of the flexible secondary tube is within a range of 2 to 5 feet long.

8. The apparatus of claim 1, wherein the flexible primary tube is an IV tube.

9. The apparatus of claim 8, wherein the flexible secondary tube is a micro bore IV tube.

10. The apparatus of claim 9, wherein the flexible secondary tube has an internal diameter that is within a range of 0.3 millimeters to 1.3 millimeters.

11. A method of manufacturing a tubing apparatus, comprising:
    providing a flexible primary tube having a first length and configured to intravenously deliver fluid to a patient, comprising:
      a first end;
      a second end opposite the first end; and
      at least one coupling port proximate the second end; and
    aligning a flexible secondary tube along its length in a direction parallel to the flexible primary tube, the flexible secondary tube having a second length, the second length being shorter than the first length, wherein the flexible secondary tube comprises:
      a proximal end configured to couple with a device to administer fluid to a patient; and
      a distal end fluidly-coupled to the flexible primary tube coupling port; and
    permanently coupling only an outer surface of the flexible primary tube to only an outer surface of the flexible secondary tube at least partially along the flexible secondary tube's length,
    wherein the flexible primary tube and the flexible secondary tube each include a uniform circumferential inner surface.

12. The method of claim 11, wherein permanently coupling the flexible secondary tube to the flexible primary tube only occurs at the secondary tube distal end.

13. The method of claim 11, wherein permanently coupling the flexible secondary tube to the flexible primary tube only occurs at the flexible secondary tube proximal end.

14. The method of claim 11, wherein permanently coupling the flexible secondary tube to the flexible primary tube only occurs at the flexible secondary tube distal and proximal ends.

15. The method of claim 11, wherein permanently coupling the flexible secondary tube to the flexible primary tube only occurs at a portion between the flexible secondary tube distal and proximal ends.

16. The method of claim 11, wherein permanently coupling the flexible secondary tube to the flexible primary tube occurs intermittently along the length of the flexible secondary tube.

17. The method of claim 11, wherein the flexible primary tube is an IV tube.

18. The method of claim 17, wherein the flexible secondary tube is a micro bore IV tube.

19. The apparatus of claim 1, wherein the first end of the primary tube is coupled to an IV bag, the second end of the primary tube is coupled to a catheter, and the proximal end secondary tube is coupled with a device to administer fluid to a patient.

20. The apparatus of claim 1, wherein a fluid passes from the proximal end to the distal end of the secondary tube faster than a fluid passes from the first end to the second end of the primary tube.

* * * * *